United States Patent [19]

Whitfill

[11] 4,213,762

[45] Jul. 22, 1980

[54] DETERMINATION OF CHROMATE ION IN DRILLING MUD FILTRATES

[75] Inventor: Donald L. Whitfill, Ponca City, Okla.

[73] Assignee: Conoco, Inc., Ponca City, Okla.

[21] Appl. No.: 969,606

[22] Filed: Dec. 14, 1978

[51] Int. Cl.² ............................................. G01N 33/24
[52] U.S. Cl. ............................... 23/230 R; 23/230 EP
[58] Field of Search ....................... 23/230 EP, 230 R; 73/155; 166/250, 252

[56] References Cited

U.S. PATENT DOCUMENTS

| | | | |
|---|---|---|---|
| 3,077,387 | 2/1963 | Boyd | 23/230 EP |
| 3,407,042 | 10/1968 | Slentz | 23/230 EP |
| 3,528,776 | 9/1970 | Hudson | 23/230 R |

FOREIGN PATENT DOCUMENTS 579864  7/1959  Canada ................................. 23/230 EP

OTHER PUBLICATIONS

Skoog et al., "Analytical Chemistry – An Introduction", Holt, Rinehart and Winston, Nov. 1965, p. 366.
Rydholm, "Pulping Processes", Interscience Publishers, 1965, pp. 210-213.

Primary Examiner—Arnold Turk
Attorney, Agent, or Firm—Bayless E. Rutherford, Jr.

[57] ABSTRACT

A method of determining the amount of chromate ion in drilling and mud filtrates containing lignosulfonates is disclosed. Briefly, the method comprises: (a) treating the filtrate with an effective amount of hydrogen peroxide to destroy any color bodies contributed by the lignosulfonate, and (b) measuring the amount of chromate ion in the filtrate by means of a spectrophotometer.

3 Claims, No Drawings

DETERMINATION OF CHROMATE ION IN DRILLING MUD FILTRATES

FIELD OF THE INVENTION

The invention is in the general field of determining chromate ion in aqueous solutions containing interferring color bodies. More particularly, the invention is in the field of determining chromate ion colorimetrically when the chromate ion is in the presence of interferring color bodies due to lignosulfonates which are commonly used as a thinner in drilling fluids.

GENERAL BACKGROUND

It is now generally recognized that drilling for oil and gas in a subterranean formation is a complex and sophisticated task. Many "arts" associated with the drilling are recognized as being of invaluable aid. For example, chemical analysis of formation water samples are valuable for numerous purposes. Among these are electric log interpretation and subsequent determination of the source of the produced water. However, there can be some question as to whether drill stem test samples are representative of actual formation water. This uncertainty is increased in cases where a high degree of mud filtrate invasion has occurred, since it is difficult to ascertain if the water is "produced formation water" or "produced mud filtrate".

A technique has been developed recently which utilizes a tracer in the mud which helps to ascertain the fraction of mud filtrate contained in the produced water.

One such technique uses sodium chromate in the mud as a tracer. While this method has had some degree of success one problem with the method occurs when chromium lignosulfonate is used in the drilling mud. The color bodies resulting from the presence of the lignosulfonate often give erroneous results in the chromate ion values determined colorimetrically.

My invention is directed to the solution of the problem created by the presence of lignosulfonate color bodies in drilling mud filtrates being subjected to determination of amount of chromate ion.

BRIEF SUMMARY OF THE INVENTION

Briefly stated, the present invention is directed to a method of determining the amount of chromate ion in an aqueous drilling mud filtrate containing organic color bodies such as lignosulfonates wherein the method comprises:

(a) treating the aqueous filtrate with an effective amount of hydrogen peroxide to destroy any color bodies contributed by the lignosulfonates, and, (b) measuring the amount of chromate ion in the filtrate by means of a spectrophotometer.

DETAILED DESCRIPTION

It is well-known in the art that aqueous drilling muds (or, as sometimes known—drilling fluids) can contain a variety of materials. For example, they can contain clays, such as bentonite, weighting materials, such as barite, and other additives. Inasmuch as it is well-known that many materials can be used, further description is not believed necessary.

My invention is applicable to aqueous drilling fluids provided they meet the following requirements: (a) contain chromate ion and (b) contain organic color bodies such as lignite or lignosulfonate.

My invention is used on the filtered aqueous drilling fluid, i.e. the filtrate. The filtrate will contain in the range of about 0.7 to about 2.8 grams per liter of chromate in combination with larger amounts of lignite or lignosulfonate (2.8 to 28).

The filtrate is treated with hydrogen peroxide (usually 30 percent solution) to remove the color bodies. The amount is determined by the amount of color bodies present. The treatment with hydrogen peroxide is continued until the color bodies are removed and a clear, colored solution results. Knowing that this is required any person skilled in the art can readily treat the filtrate to the degree required to remove color bodies. In order to provide a more complete teaching, an example procedure that has proven effective is as follows:

1. Measure 5 ml of sample with a delivery pipette into a 50-ml Erlenmeyer flask (a critical measurement).
2. Add 5 ml of 30 percent $H_2O_2$ (hydrogen peroxide). Measure with a graduated cylinder (it is not critical to measure the exact amount).
3. Place sample on a hot plate adjusted below 212° F. until decomposition reaction starts.
4. Set sample off the hot plate until the reaction slows somewhat to prevent foaming over.
5. Place back on the hot plate until the $H_2O_2$ decomposition is completed (no more bubbles).
6. Add a few ml of water and increase the temperature to boiling. Boil for 5-10 minutes.
7. Remove from the hot plate and cool to room temperature. Add sufficient water (after cooling) to reach a total volume of 50 ml (easier to do in an Erlenmeyer with volumetric markings on the sides). This is a critical measurement.

The amount of chromate ion in the treated filtrate is determined using a spectrophotometer by known techniques.

While a variety of spectrophotometers can be used my work was done using a HACH DR/2 Spectrophotometer.

The standard procedure for measuring sodium chromate on this instrument is as follows:

1. Take a water sample by filling a clean 25-ml graduated cylinder to the 25-ml mark. Pour the sample into a clean sample cell. See Note A.
2. If the water sample is orange, add the contents of one HACH Neutralizing Powder Pillow or 1 drop of 5 M NaOH and swirl to mix. See Note B.
3. Fill another sample cell with about 25 ml of clear, colorless water and place it in the cell holder. Insert the Sodium Chromate (Direct Colorimetric Method) Meter Scale in the meter and adjust the Wavelength Dial to 460 nm. Adjust the LIGHT CONTROL for a meter reading of zero mg/l. See Note C.
4. Place the prepared sample in the cell holder and read the mg/l sodium chromate ($Na_2CrO_4$).

Notes

A. Filtering is recommended for turbid water samples. Large amounts of turbidity will cause high readings.

B. The test measures the intensity of the alkaline yellow color directly. The Neutralizing Powder Pillow is necessary only if the sample is orange or yellow-orange.

C. The correct wavelength setting is important in this determination. For maximum accuracy the Wavelength Dial should first be adjusted to the correct scale reading (near 460 nm) using Standard Sodium Chromate Solution, 1000 mg/l as $Na_2CrO_4$, and a reagent blank.

In my work a 5.0 ml sample was treated with hydrogen peroxide and then diluted to a final volume of 50 ml. The 50 ml sample was used in the spectrophotometer. Because a 10:1 dilution was used the meter reading value was multiplied by 10.

In order to illustrate the nature of the present invention still more clearly the following examples will be given. It is to be understood, however, that the invention is not to be limited to the specific conditions or details set forth in these examples except insofar as such limitations are specified in the appended claims.

EXAMPLE 1

This example illustrates the accuracy obtained in determining chromate concentration by means of the spectrophotometer using the procedure described in the foregoing. The sodium chromate concentration was measured on six samples of an aqueous solution containing 1000 mg/l of sodium chromate. The results were as follows (mg/l): 880, 900, 800, 700 and 825. The mean and standard deviation were as follows:

$$\bar{x} = 821 \pm 79$$

EXAMPLE 2

This example illustrates the beneficial effects of hydrogen peroxide treatment in accordance with my invention.

A. Solution A was an aqueous solution containing the following: 1000 mg/l of $Na_2CrO_4$ and 1 pound per barrel (2850 mg/l) of chromium lignosulfonate which contributed 450 mg/l of $Na_2CrO_4$. Accordingly, the solution contained a total of 1450 mg/l of $Na_2CrO_4$. The results of chromate determination on an untreated sample and on a hydrogen peroxide treated sample are shown in the following table.

B. Solution B was a filtrate from a drilling fluid containing:

1.5 ppb* chromium lignosulfonate which contributed 110 mg/l $Na_2CrO_4$ 0.25 ppb (710 mg/l) $Na_2CrO_4$ 20.0 ppb bentonite 1.0 ppb sodium hydroxide

*ppb=pounds per barrel

The calculated $Na_2CrO_4$ amount was 820 mg/l. The results of chromate determination on an untreated sample and on a hydrogen peroxide treated sample are shown in the following table.

TABLE I

| | Calculated mg/l $Na_2CrO_4$ | Untreated Sample Apparent mg/l $Na_2CrO_4$ | Treated Sample mg/l $Na_2CrO_4$ |
|---|---|---|---|
| Solution A | 1450 | 9400 | 1375 |
| Solution B | 820 | 4800 | 700 |

Two conclusions result from this example:

(1) the presence of lignosulfonate provides very erroneous chromate results, (2) treatment with hydrogen peroxide to remove the color bodies due to the lignosulfonate provides chromate results substantially within the accuracy of the colorimetric method of determining chromate ion.

Thus, having described the invention in detail, it will be understood by those skilled in the art that certain variations and modifications may be made without departing from the spirit and scope of the invention as defined herein and in the appended claims.

I claim:

1. A method of determining the amount of chromate ion in an aqueous drilling mud filtrate containing organic color bodies such as lignosulfonate wherein the method comprises:

(a) treating the aqueous filtrate with an effective amount of hydrogen peroxide to destroy said color bodies, and (b) measuring the amount of chromate ion in the filtrate by means of a spectrophotometer.

2. The method of claim 1 wherein the mud filtrate contains about 0.7 to about 2.8 grams per liter of chromate ion and about 2.8 to about 28 grams per liter of lignosulfonate.

3. The method of claim 1 wherein the mud filtrate comes from a drilling mud containing bentonite.

* * * * *